(12) United States Patent
Edwards et al.

(10) Patent No.: US 10,835,840 B2
(45) Date of Patent: Nov. 17, 2020

(54) METHODS FOR IN SITU SEPARATION OF MIXTURES

(71) Applicant: INTERNATIONAL SCIENTIFIC PTY LTD, Leederville (AU)

(72) Inventors: Jeffrey Edwards, Leederville (AU); Matthew McIldowie, Craigie (AU)

(73) Assignee: INTERNATIONAL SCIENTIFIC PTY LTD., Leederville (AU)

( * ) Notice: Subject to any disclaimer, the term of this patent is extended or adjusted under 35 U.S.C. 154(b) by 323 days.

(21) Appl. No.: 15/579,752

(22) PCT Filed: Jun. 17, 2016

(86) PCT No.: PCT/AU2016/000213
§ 371 (c)(1),
(2) Date: Dec. 5, 2017

(87) PCT Pub. No.: WO2016/201491
PCT Pub. Date: Dec. 22, 2016

(65) Prior Publication Data
US 2018/0169543 A1    Jun. 21, 2018

(30) Foreign Application Priority Data

Jun. 19, 2015  (AU) .............................. 2015902376

(51) Int. Cl.
*A61K 8/67*   (2006.01)
*B01D 17/04*  (2006.01)
(Continued)

(52) U.S. Cl.
CPC ............ *B01D 17/041* (2013.01); *A61K 8/675* (2013.01); *A61K 8/678* (2013.01); *A61Q 19/00* (2013.01);
(Continued)

(58) Field of Classification Search
CPC ..................................................... A61K 8/675
See application file for complete search history.

(56) References Cited

U.S. PATENT DOCUMENTS

| | | | |
|---|---|---|---|
| 7,762,269 B2 | 7/2010 | Wyatt et al. | |
| 2008/0031907 A1* | 2/2008 | Tamarkin ............... | A61K 8/046 424/401 |

(Continued)

FOREIGN PATENT DOCUMENTS

WO    WO-2014/043404 A1    3/2014

OTHER PUBLICATIONS

International Application No. PCT/AU2016/000213, International Search Report and Written Opinion, dated Oct. 4, 2016.
(Continued)

*Primary Examiner* — Benjamin J Packard
(74) *Attorney, Agent, or Firm* — Marshall, Gerstein & Borun LLP

(57) ABSTRACT

The present invention provides a method for the separation of a mixture having a first component and a second component, the method comprising the steps of: (a) applying at least two destabilizing energy forms to the mixture to destabilize the mixture, wherein the destabilizing energy forms are chosen from the list comprising: mechanical shear force, thermal energy, and/or surface energy; and (b) applying at least one enriching energy form to the mixture to form a first region that is enriched in a first component relative to the second component and a second region that is enriched in the second component relative to the first component, wherein the enriching energy form is surface energy.

11 Claims, 6 Drawing Sheets

Figure 2:
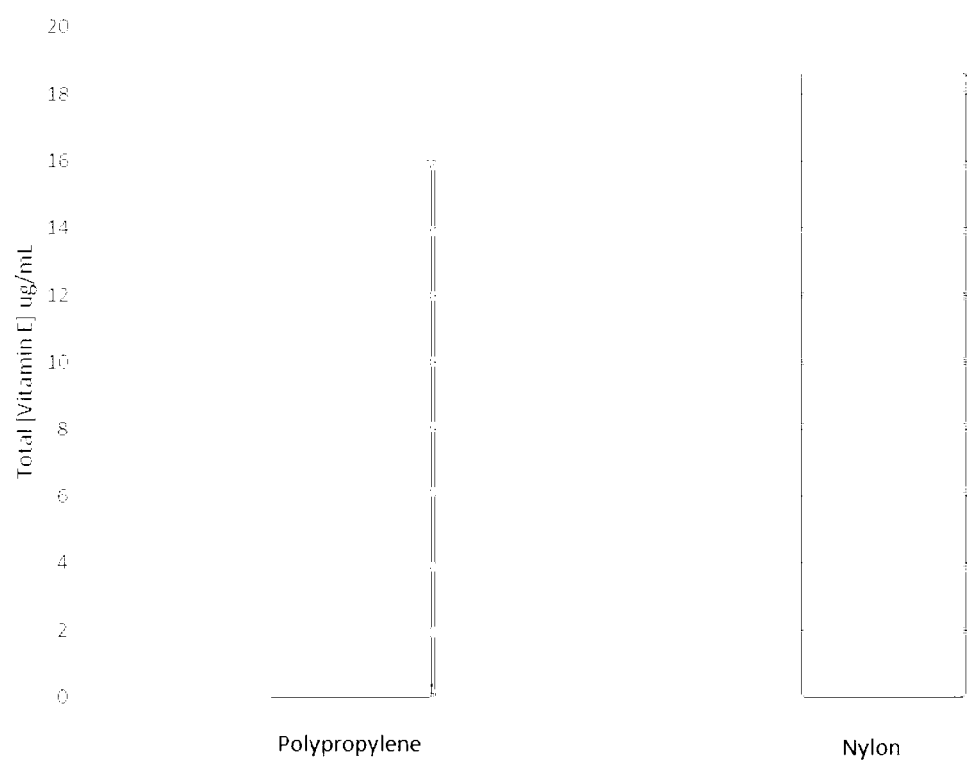
Figure 3:
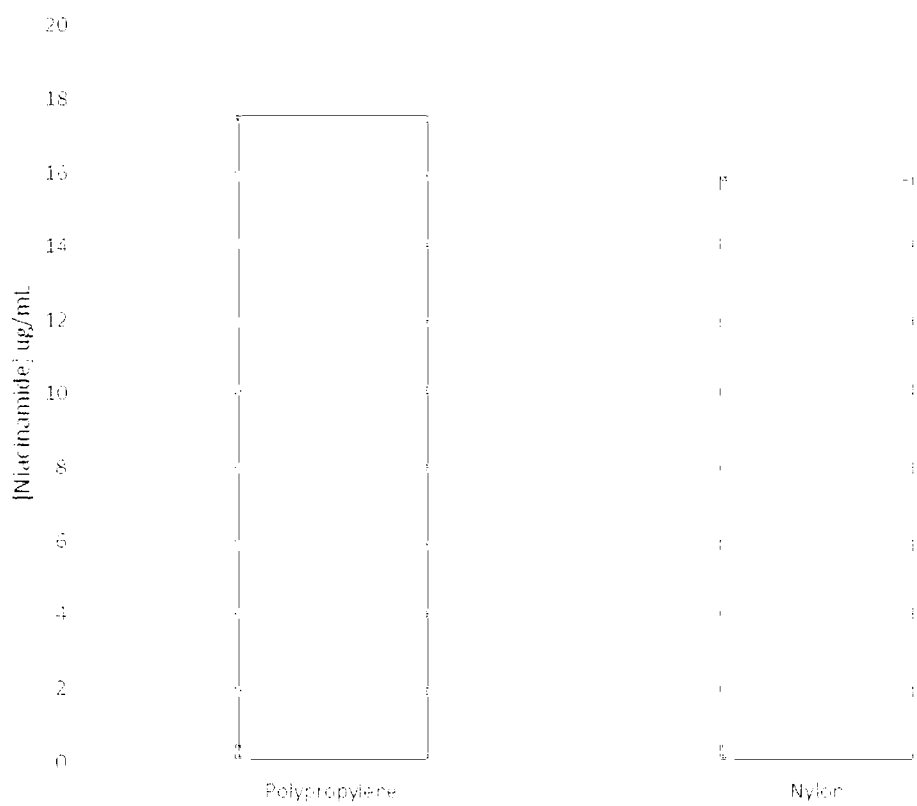
Figure 4:
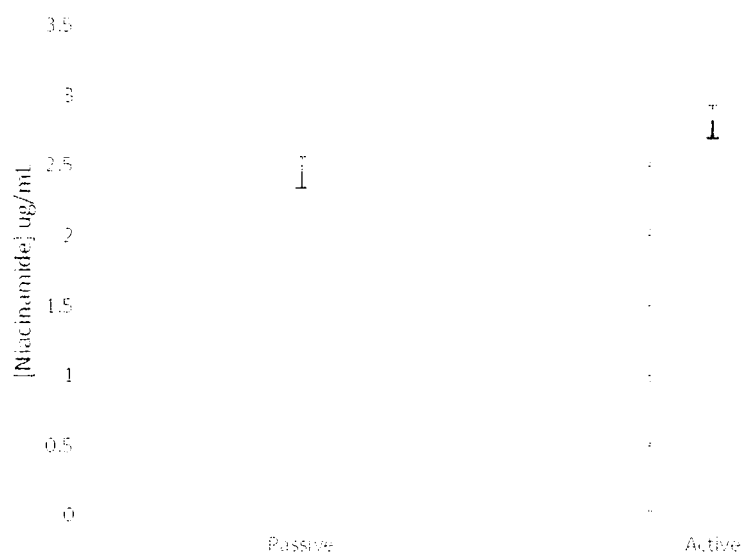

(51) Int. Cl.
   *B01D 19/00*    (2006.01)
   *A61Q 19/00*    (2006.01)
(52) U.S. Cl.
   CPC ......... *B01D 17/042* (2013.01); *B01D 17/047* (2013.01); *B01D 19/0047* (2013.01); *A61K 2800/87* (2013.01)

(56) References Cited

U.S. PATENT DOCUMENTS

| | | |
|---|---|---|
| 2008/0142495 A1 | 6/2008 | Des Garets |
| 2013/0160785 A1 | 6/2013 | Thevenet et al. |
| 2014/0216490 A1 | 8/2014 | Wilson et al. |
| 2014/0353263 A1 | 12/2014 | Stanfel et al. |

OTHER PUBLICATIONS

International Application No. PCT/AU2016/000213, International Preliminary Report on Patentability, dated Dec. 19, 2017.
Lademann et al., The tape stripping procedure—evaluation of some critical parameters, Eur. J. Pharm. Biopharm., 72(2):317-23 (2009).

\* cited by examiner

```
-   S   -   S   -   S   -   S   -   S   -
N   -   N   -   N   -   N   -   N   -   N
-   S   -   S   -   S   -   S   -   S   -
N   -   N   -   N   -   N   -   N   -   N
-   S   -   S   -   S   -   S   -   S   -
N   -   N   -   N   -   N   -   N   -   N
```

Figure 1

METHODS FOR IN SITU SEPARATION OF MIXTURES

TECHNICAL FIELD

A method and device to separate a mixture, which further allows the separated components of the mixture to be enriched in various in situ formed regions.

BACKGROUND ART

The following discussion of the background art is intended to facilitate an understanding of the present invention only. The discussion is not an acknowledgement or admission that any of the material referred to is or was part of the common general knowledge as at the priority date of the application.

The attractive forces that exist between molecules are known as intermolecular forces. These forces are responsible for the stability and the physical state of matter, including the stability and state of mixtures used for skin care purposes. A mixture is a material system made up of a physical combination of two or more different components which are mixed but are not combined chemically; the identities of the components are retained. They are a product of mechanical blending or mixing of components such as elements and compounds, without chemical bonding between the components or chemical changes to the components, so that each component retains its own chemical properties and makeup. Mixtures include emulsions, suspensions, or colloids.

Mixtures gain their physical properties and stability due to intermolecular forces. The intermolecular forces include: ion-dipole interactions (ion-dipole and ion-induced dipole forces); hydrogen bonding; dipole moments; Lennard-Jones potential; polarizability; and Van Der Waals interactions (Keesom [permanent-permanent dipoles] interactions; Debye [permanent-induced dipoles] forces; London dispersion forces). The London dispersion force is the weakest intermolecular force. It is a temporary attractive force that results when the electrons in two adjacent atoms occupy positions that make the atoms form temporary dipoles.

Emulsions are a subset of mixtures. They are a dispersion of normally immiscible liquid components combined together such that each retains its own separate physicochemical properties. In an emulsion, one liquid (the dispersed or internal phase) is dispersed in the other (the continuous or external phase). The boundary between the two phases is called the interface. Two liquids can form different types of emulsions. As an example, oil and water can form, first, an oil-in-water emulsion, wherein the oil is the dispersed phase, and water is the dispersion medium. Second, they can form a water-in-oil emulsion, wherein water is the dispersed phase and oil is the external phase. Multiple emulsions are also possible, including a "water-in-oil-in-water" emulsion and an "oil-in-water-in-oil" emulsion.

In order to create a stable emulsion, work must be done to overcome the interfacial tension between the two phases. This can be achieved by mixing; however mixing even at very high rates may not be enough to provide long term stability. An emulsifier or combination of emulsifiers is generally needed to stabilize the droplets of the dispersed phase.

Suspensions are a subset of mixtures. A suspension is a heterogeneous mixture containing solid particles that are sufficiently large for sedimentation. Usually they must be larger than one micrometer. The internal phase (solid) is dispersed throughout the external phase (fluid) through mechanical agitation, often with the use of certain excipients or suspending agents. The particles of a suspension will settle over time if left undisturbed, in contrast to a colloid. A colloid is a mixture in which microscopically dispersed insoluble particles are suspended throughout another substance. A colloid has a dispersed phase (the suspended particles) and a continuous phase (the medium of suspension). To qualify as a colloid, the mixture must be one that does not settle or would take a very long time to settle appreciably.

Mixtures, including emulsions, colloids and suspensions, are commonly used during the manufacture of cosmetic and skincare formulations. In order to maintain the shelf-life of a cosmetic or skincare product in the form of a mixture, the mixture must be highly stable. In some situations, such as the application of a cosmetic formulation to skin, it is nevertheless desirable that components such as active agents exit the mixture. However, this very stability reduces the likelihood that components will be able to exit the mixture. In situ separation of a stable mixture (i.e. separation of the mixture once applied to the skin), would assist in this process.

There is therefore a need for methods to separate a mixture in situ, during application to the skin, to allow improved partitioning and diffusion of components from the mixture.

The present invention seeks to provide an improved or alternative method for the separation of a mixture in situ. In addition or alternatively, the invention seeks to provide an improved or alternative method for the enrichment of separate components of the destabilized mixture in in situ-formed regions as a means of further enhancing partitioning, diffusion and occlusion, all of which are beneficial to the efficacy of the mixture.

SUMMARY OF INVENTION

The present invention provides a method for the separation of a mixture having a first component and a second component, the method comprising the steps of:
  a) applying at least two destabilizing energy forms to the mixture to separate the mixture, wherein the destabilizing energy forms are chosen from the list comprising: a weak magnetic field, mechanical shear force, thermal energy, and/or surface energy;
  b) applying at least one enriching energy form to the mixture to form a first region that is enriched in the first component relative to the second component and a second region that is enriched in the second component relative to the first component, wherein the enriching energy form is chosen from the list comprising: a weak magnetic force, and/or surface energy.

Preferably the method of separation of a mixture involves applying at least two destabilizing energy forms and at least two enriching energy forms.

More preferably the method of separation of a mixture involves applying at least two destabilizing energy forms; and surface energy as the enriching energy form.

More preferably the method of separation of a mixture involves applying at least two destabilizing energy forms wherein one of destabilizing energy forms is surface energy; and (ii) surface energy as the enriching energy form.

Preferably the mixture is applied to a surface, more preferably a skin surface, before separation occurs.

The present invention further provides an applicator device for the separation of a mixture having a first component and a second component said device comprising:
  a) means to generate at least two destabilizing energy forms chosen from the list comprising: a weak magnetic field, mechanical shear force, thermal energy, and/or surface energy;
  b) a means to generate at least one enriching energy form chosen from the list comprising: a weak magnetic force, surface energy
wherein during use the destabilizing energy forms destabilize the mixture and the enriching energy form forms a first region that is enriched in the first component relative to the second component and a second region that is enriched in the second component relative to the first component.

Preferably the applicator device for separation of a mixture comprises means for generating at least two destabilizing energy forms and means for generating at least two enriching energy forms.

More preferably the applicator device for separation of a mixture comprises means for generating at least two destabilizing energy forms; and means for generating surface energy as the enriching energy form.

More preferably the applicator device for separation of a mixture comprises means for generating at least two destabilizing energy forms wherein one of destabilizing energy forms is surface energy; and means for generating surface energy as the enriching energy form.

Preferably the mixture is applied to a surface, more preferably a skin surface, before the steps of
  a) applying at least two destabilizing energy forms to the mixture to separate the mixture, wherein the destabilizing energy forms are chosen from the list comprising: a weak magnetic field, mechanical shear force, thermal energy, and/or surface energy; and
  b) applying at least one enriching energy form to the mixture to form a first region that is enriched in the first component relative to the second component and a second region that is enriched in the second component relative to the first component, wherein the enriching energy form is chosen from the list comprising: a weak magnetic force, and/or surface energy;
are performed.

The present invention further provides a method for the destabilization of a mixture having a first component and a second component, after application of the mixture to a surface, the method comprising the steps of:

c) applying at least two destabilizing energy forms to the mixture to destabilize the mixture, wherein the destabilizing energy forms are chosen from the list comprising: a weak magnetic field, mechanical shear force, thermal energy, and/or surface energy;

d) applying at least one enriching energy form to the mixture to form a first region that is enriched in a first component relative to the second component and a second region that is enriched in the second component relative to the first component, wherein the enriching energy form is chosen from the list comprising: a weak magnetic force, and/or surface energy.

The present invention further provides an applicator device for the destabilization of a mixture having a first component and a second component after application of the mixture to a surface, said device comprising:

c) means to generate at least two destabilizing energy forms chosen from the list comprising: a weak magnetic field, mechanical shear force, thermal energy, and/or surface energy;

d) a means to generate at least one enriching energy form chosen from the list comprising: a weak magnetic force, surface energy wherein during use the destabilizing energy forms destabilize the mixture and the enriching energy form forms a first region that is enriched in a first component relative to the second component and a second region that is enriched in the second component relative to the first component.

BRIEF DESCRIPTION OF THE DRAWINGS

The description will be made with reference to the accompanying drawings in which:

FIG. 1 is a diagrammatic representation of an example complex weak magnetic field in the form of a flexible magnetic film according to the present invention.

FIG. 2 is a graph of the loading of Vitamin E in the skin after application in the presence of surface free energy determined by tape stripping.

FIG. 3 is a graph of the loading of niacinamide in the skin in the presence of surface free energy determined by tape stripping.

FIG. 4 is a graph of the loading of niacinamide in the skin in the presence of a weak magnetic field determined by tape stripping.

FIG. 5 is a graph of the loading of niacinamide in the skin in the presence of mechanical shear force determined by tape stripping.

FIG. 6 is a graph of the loading of niacinamide in the skin in the presence of mechanical shear force plus surface energy determined by tape stripping.

DESCRIPTION OF THE INVENTION

Detailed Description of the Invention

"Skin" and "dermis", "dermal surface" and "surface" are used interchangeably in the present invention. "Skin" means the outermost protective covering of mammals that is composed of cells such as keratinocytes, fibroblasts and melanocytes. Skin includes an outer epidermal layer and an underlying dermal layer. Skin includes mucosal surfaces.

A "mixture" is a material system made up of a physical combination of two or more different components which are mixed but are not combined chemically; the identities of the components are retained. They are a product of mechanical blending or mixing of components such as elements and compounds, without chemical bonding between the components or chemical changes to the components, so that each component retains its own chemical properties and makeup. Mixtures include emulsions, suspensions, or colloids.

A mixture is in a high energy state, created by aggressive mixing during manufacture. A mixture will remain in this state as long as the intermolecular forces act to keep the components in that mixed state. If sufficient energy is added to elevate a stable mixture beyond its transitional point, the intermolecular forces holding the mixture in the stable high energy state will be overcome and the mixture will destabilize and separate into its original multi-component parts, as there is a tendency in nature for systems to return to their lowest energy forms.

The present invention provides a method for the separation of a mixture having a first component and a second component, the method comprising the steps of:

a) applying at least two destabilizing energy forms to the mixture to destabilize the mixture, wherein the destabilizing energy forms are chosen from the list comprising: a weak magnetic field, mechanical shear force, thermal energy, and/or surface energy;

b) applying at least one enriching energy form to the mixture to form a first region that is enriched in the first component relative to the second component and a second region that is enriched in the second component relative to the first component, wherein the enriching energy form is chosen from the list comprising: a weak magnetic force, and/or surface energy.

Preferably the method of separation of a mixture involves applying at least two destabilizing energy forms and at least two enriching energy forms.

More preferably the method of separation of a mixture involves applying (i) at least two destabilizing energy forms; and (ii) surface energy as the enriching energy form.

More preferably the method of separation of a mixture involves applying (i) at least two destabilizing energy forms wherein one of destabilizing energy forms is surface energy; and (ii) surface energy as the enriching energy form.

Preferably the mixture is applied to a surface, more preferably a skin surface, before separation occurs.

The mixture may be applied on the dermal surface or skin by use of an applicator device. The mixture may be applied to the skin, and then spread over the skin using the applicator device, or the mixture may be applied to the applicator device and then the applicator device with the mixture on it may be applied to the skin to spread the mixture. The applicator device can be moved or rubbed, either manually or by motorised action over the dermal surface.

Examples of applicator devices include roller balls; pads such as fabric pads or sponges; solid surface applicators such as sticks, wands, paddles etc.

The applicator device may contain a means to generate the destabilizing energy forms and the enriching energy forms of the present invention. For example, the materials that form the area of the applicator device that come in contact with the skin may be chosen such that they generate a destabilizing energy form and/or an enriching energy form (for example a material with a specific surface force or a material that generates a weak magnetic field). In addition or alternatively, the applicator may contain means to generate a destabilizing energy form and/or an enriching energy form (for example a magnetic film, or a heating element) in proximity to the area of the applicator device that comes in contact with the skin.

The applicator device that applies the mixture may be moved over the surface of the skin or dermal barrier. The movement may be either through manual operation or through mechanical means. Where movement of the applicator is delivered through manual operation (i.e. through normal consumer actions such as rubbing or brushing), the frequency will be in the order of 1 Hz to 5 Hz. In the alternate, where movement is delivered through mechanical or electrical means (such as in the form of a roller ball driven or rotated by a motor) the oscillation should be in the order of approximately 100 and 8,000 Hz. If the movement is delivered through mechanical or electrical means, the applicator device includes a means for moving at least a portion of the applicator over the dermal barrier. Such a means will include any mechanism, electronic or mechanical, adapted for reciprocal or rotational movement of at least a portion of the applicator. That portion of the applicator device that is subject to the reciprocal or rotational movement should be at least the area of the applicator device that comes in contact with the skin. Such a means will include any mechanism, electronic or mechanical, adapted for reciprocal or rotational movement of at least a portion of the applicator. For example, the applicator may contain a drive mechanism that is capable of reciprocal movement, preferably reciprocal movement of the area of the applicator device that comes in contact with the skin.

As used herein, rotational includes movement in an arc-like, semi-circular, circular or orbital manner.

Energy Forms for Destabilization

Preferably, the destabilizing energy forms used to separate the mixture are sufficient to overcome the intermolecular forces within the mixture. The destabilizing energy forms elevate the energy state of the mixture beyond its transitional point, thus overcome the intermolecular forces that hold the mixture in its stable state. This then causes the mixture to return to its original multi-component form without altering the chemical structure, pharmacology or function of the individual components.

Preferably the mixture is destabilized by the destabilizing energy forms to its individual components after or during application to the skin. Thus the mixture is destabilized in situ after application to the skin.

Mechanical Shear Force

Preferably, the destabilizing energy form is provided in the form of mechanical shear force. The shear force may be generated by use of an applicator to spread the mixture onto a surface, such as a dermal or skin surface. Preferably the mixture is spread on the surface in a thin film.

Preferably the thin film of mixture on the surface is about 0.1 mm to 1 mm in thickness. For example, the thin film may be 0.2 mm, 0.3 mm, 0.4 mm, 0.5 mm, 0.6 mm, 0.7 mm, 0.8 mm, or 0.9 mm.

The mechanical shear force is preferably applied at between about 150 Pa and 20,000 Pa. For example, the shear force may be about 150 Pa, 200 Pa, 300 Pa, 400 Pa, 500 Pa, 600 Pa, 700 Pa, 800 Pa, 900 Pa, 1,000 Pa, 2,000 Pa, 3,000 Pa, 4,000 Pa, 5,000 Pa, 6,000 Pa, 7,000 Pa, 8,000 Pa, 9,000 Pa, 10,000 Pa, 11,000 Pa, 12,000 Pa, 13,000 Pa, 14,000 Pa or 15,000 Pa, 16,000 Pa, 17,000 Pa, 18,000 Pa, 19,000 Pa, or 20,000 Pa. The range may be 150 Pa to 1,000 Pa, 300 Pa to 8,000 Pa, or 400 Pa to 12,000 Pa. Preferably the range is 400 Pa to 12,000 Pa.

The mechanical shear force may be applied to the mixture on the dermal surface by use of an applicator. The mixture may be applied to the skin, and then spread over the skin using an applicator, or the mixture may be applied to the applicator and then the applicator with the mixture on it may be applied to the skin to spread the mixture.

The mechanical shear force assists in the destabilization of the mixture by creating a thin film of the mixture across the skin, therefore enhancing the surface area exposed to the skin, the air, the other destabilizing energy forms and/or the enriching energy forms.

Weak Magnetic Field

The destabilizing energy form may be provided in the form of a weak magnetic field. By weak magnetic field, it is meant that the magnetic field used to destabilize the mixture is less than about 100 mT (or 1000 Gauss). More preferably, the weak magnetic field is between 0.1 mT and 50 mT (between 1 and 500 Gauss). "Magnetic field" and "magnetic flux density" are used interchangeably herein and refer to the vector field measured in Teslas or Gauss.

Preferably the weak magnetic field is provided by a magnetic film. Preferably the Preferably the magnetic film is a flexible magnetic film. Preferably the magnetic film comprises magnetic elements, particles, fragments, or flakes disposed in a solid or semi-solid matrix, preferably a flexible solid or semi-solid matrix.

The magnetic film may be present within the applicator device, in proximity to the area of the applicator device that comes in contact with the skin to spread the mixture over the skin. Alternatively, the material that forms the area of the applicator device that comes in contact with the skin may generate a weak magnetic field.

In the magnetic film, each individual magnetic element provides diamagnetic repulsion to the components which are to be transported across the skin barrier, whilst the horizontal flux between the various magnetic elements acts to polarize the dielectric properties of the target skin tissue, inducing permeation changes.

Generally, the magnetic elements of the magnetic film have a horizontal offset between centres of between 1 and 10 millimetres, preferably between 2 and 8 millimetres, more preferably between 3 and 7 millimetres. The horizontal offsets may be 1 mm, 2 mm, 3 mm, 4 mm, 5 mm, 6 mm, 7 mm, 8 mm, 9 mm or 10 mm, or any range between.

As a result, the magnetic elements may be disposed at a repetition rate of between 1 and 10 elements per centimetre, preferably between 1 and 6 elements per centimetre more preferably 1.5 and 4 elements per centimetre. The magnetic elements may be disposed at a repetition rate of 1 elements per centimetre, 1.5 elements per centimetre, 2 elements per centimetre, 2.5 elements per centimetre, 3 elements per centimetre, 3.5 elements per centimetre, 4 elements per centimetre, 4.5 elements per centimetre, 5 elements per centimetre, 5.5 elements per centimetre, 6 elements per centimetre, 6.5 elements per centimetre, 7 elements per centimetre, 7.5 elements per centimetre, 8 elements per centimetre, 8.5 elements per centimetre, 9 elements per centimetre, 9.5 elements per centimetre, or 10 elements per centimetre, or any range between.

Preferably, the poles of the magnetic elements in a particular spatial region are between 1.0 mm to 10 mm apart, more preferably the poles are between 1.0 mm to 5.0 mm apart. For example, the poles may be 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0 mm apart, or any range between.

In another aspect of the invention, the magnetic flux density of each magnetic pole of the magnetic elements is below about 100 mT. Preferably, the flux density of each pole is between about 0.1 mT to about 50 mT, most preferably about 12 mT to 45 mT. For example, the magnetic flux density may be 0.1 mT, 1 mT, 5 mT, 10 mT, 11 mT, 12 mT, 13 mT, 14 mT, 15 mT, 20 mT, 25 mT, 30 mT, 35 mT, 40 mT, 45 mT, 50 mT, 55 mT, 60 mT, 65 mT, 70 mT, 75 mT, 80 mT, 85 mT, 90 mT, 95 mT or 100 mT, or any range between.

The skilled reader will be aware that 100 mT is equivalent to 1000 Gauss. Therefore, the magnetic flux density of each magnetic pole of the magnetic elements is preferably below 1000 Gauss, more preferably between about 1 Gauss and about 1000 Gauss. More preferably, the flux density of each pole is between about 1 Gauss and about 500 Gauss.

In another aspect, the difference or delta flux between the magnetic flux density of two adjacent poles of opposite polarity is between about 0.2 mT and about 200 mT. More preferably, the difference between the magnetic flux density of two adjacent poles of opposite polarity is between about 10 mT to about 140 mT, most preferably about 10 mT to 50 mT. The delta flux may therefore be 2 mT, 5 mT, 10 mT, 20 mT, 25 mT, 30 mT, 35 mT, 40 mT, 45 mT, 50 mT, 55 mT, 60 mT, 65 mT, 70 mT, 75 mT, 80 mT, 85 mT, 90 mT, 95 mT, 100 mT, 105 mT, 110 mT, 115 mT, 120 mT, 130 mT, 140 mT, 150 mT, 160 mT, 170 mT, 180 mT, 190 mT, 200 mT, or any range between.

Preferably, the magnetic elements of the magnetic material have the following parameters:

i) a horizontal off-set of between about 1 and 10 millimetres, 2 and 8 millimetres, or 3 and 7 millimetres; and/or ii) a repetition rate of about 1 and 10 elements per centimetre, 1 and 6 elements per centimetre or 1.5 and 4 elements per centimetre; and/or iii) the poles of the magnetic elements in a particular spatial region are between about 1.0 mm to 10 mm apart, or 1.0 mm to 5.0 mm apart; and/or iv) the magnetic flux of each magnetic pole of the magnetic elements is between about 0.1 mT and 100 mT, 1 mT to about 60 mT, or 12 mT to 45 mT; and/or v) the delta flux between the magnetic flux of two adjacent poles of opposite polarity is between about 0.2 mT and 200 mT, 20 mT to 140 mT, or 20 mT to 90 mT.

The magnetic elements in the magnetic film may be arranged in a linear fashion, with rows of N and S elements forming a simple linear pattern.

The magnetic elements in the magnetic film may alternatively generate a complex field that has three separate polarities—neutral, north and south. FIG. 1 is a diagrammatic representation of an example field, wherein neutral [shown as -] has magnetic flux of between 0-30 mT, north [shown as N] has magnetic flux density of between 25 mT and 50 mT and south [shown as S] has magnetic flux density of between −25 mT and −50 mT. Arrangement of the three polarities creates a series of S, N, S, N diamond shapes, with a neutral flux in the centre, linked together by proximity with the adjoining diamond shape.

For example, across line one of FIG. 1, the fluxes might be 20 mt, −45 mT, 20 mt, −45 mT; across line two it might be 45 mT, 20 mT, 45 mT, 20 mT.

The strongest magnetic gradient would be located between the north and south poles. Preferably the gradient is between 50 mT and 100 mT, more preferably 90 mT.

To create such a complex field on a magnetic film, one may start with a standard linear parallel flux pattern of N, 5, N, S wherein each flux is, for example, 45 mT (ie the N are all 45 mT, and the S are all −45 mT). This may then be crossed at 90 degrees with another linear parallel N, S, N, S flux pattern of, for example, 25 mT (ie the N are all 25 mT, and the S are all −25 mT). Where the N and S of the two flux patterns overlap, the magnetic fluxes cancel each other out, resulting in a neutral flux of, for example, 20 mT (eg a 45 mT N cancels out a −25 mT S to leave a neutral 20 mT flux). Such complex fields are preferably generated by overlaying two linear arrays at an angular offset of between 1 degree and 90 degrees, for example 5, 10, 15, 20, 25, 30, 35, 40, 45, 50, 55, 60, 65, 70, 75, 80, 85 or 90 degree angular offset.

Preferably the magnetic film is between 0.5 and 1.2 mm thickness.

Preferably, the magnetic elements or particles of the magnetic film are disposed in a solid or semi-solid matrix or base. Preferably the solid or semi-solid matrix or base is a flexible solid or semi-solid matrix or base. The solid or semi-sold matrix may comprise a flexible matrix chosen from the list comprising, but not limited to: rubber, silicone, polyethylene terephthalate (PET), polyethylene naphthalate (PEN), polyethersulphone (PES), polyimide (P1), polydimethylsiloxane (PDMS), graphene, poly (methyl methacrylate) (PMMA). The magnetic film may be produced by combining pre-magnetised elements with the solid or semi-solid matrix, or non-magnetised elements may be provided in a solid or semi-solid matrix and the required magnetic pattern is then impressed upon the elements.

The magnetic film may be constructed using a range of magnetic materials exhibiting ferromagnetic properties. Preferably, the material is a ferromagnetic material such as an iron compound (e.g. a ferrite such as barium ferrite, magnetite, or mild steel), a cobalt material, a strontium material, a barium material or a nickel material; optionally with a metalloid component such as boron, carbon, silicon, phosphorus or aluminium. Alternately, rare-earth materials such as neodymium or samarium-cobalt may also be used.

The weak magnetic field will preferably act on diamagnetic and/or paramagnetic components of the mixture. Diamagnetism is the property of an object or material which causes it to create a magnetic field in opposition to an externally applied magnetic field, thus causing a repulsive effect. Paramagnetism is the property of an object or material which causes it to create a magnetic field in the direction of an externally applied magnetic field, thus causing an attractive effect.

Manipulating the magnetic flux within certain limits increases the diamagnetic repulsion of some components of the mixture away from the magnetic source and towards the skin barrier and increases the paramagnetic attraction of other components of the mixture towards the magnetic source and away from the skin. In this way, diamagnetic repulsion/paramagnetic attraction provides a means of adding directionality and mobility to molecules during diffusion.

Without being bound by any particular theory, it is believed that in general, increasing the magnetic flux beyond a certain limit does not lead to a continued increase in diamagnetic/paramagnetic enhanced flow of components. Instead, above a certain level the increased magnetic flux instead leads to increased thermal noise and or other disordering processes that act contrary to diamagnetic repulsion/paramagnetic attraction induced diffusion enhancement. This thermal noise causes an increase in the random movement of molecules that can overwhelm the diamagnetic repulsion/paramagnetic attraction effect created by the presence of a magnetic field. Increasing the magnetic flux to very high levels, or the use of strong magnets such as those with a magnetic flux density of 5,000-50,000 Gauss or more, will not work in providing suitable diamagnetic repulsion/paramagnetic attraction, as they increase the entropic motion of the components, and this increase in the randomness of the motion of the elements results in the components not moving in the specific directions desired.

Preferably, the mixture being subject to the destabilizing energy form provided in the form of a weak magnetic field contains one or more components having a diamagnetic susceptibility of between $-20\times10^{-6}$ emu (electro-magnetic units) and $-300{,}000\times10^{-6}$ emu units. Diamagnetic components have a relative magnetic permeability that is less than or equal to 1, and therefore a magnetic susceptibility less than or equal to 0 and are therefore repelled by magnetic fields. For example, the diamagnetic susceptibility of the components of the mixture may be $-20\times10^{-6}$ emu, $-50\times10^{-6}$ emu, $-100\times10^{-6}$ emu, $-200\times10^{-6}$ emu, $-500\times10^{-6}$ emu, $-1{,}000\times10^{-6}$ emu, $-2{,}000\times10^{-6}$ emu, $5{,}000\times10^{-6}$ emu, $-10{,}000\times10^{-6}$ emu, $-50{,}000\times10^{-6}$ emu, $-100{,}000\times10^{-6}$ emu, $-150{,}000\times10^{-6}$ emu, $-200{,}000\times10^{-6}$ emu, $-300{,}000\times10^{-6}$ emu or any value in between. As each different component of the mixture has a different diamagnetic susceptibility, no preferred values can be determined.

Preferably, the mixture being subject to the destabilizing energy form provided in the form of a weak magnetic field contains one or more components having a paramagnetic susceptibility of between 0 and $1\times10^{4}$ emu units. Paramagnetic components have a relative magnetic permeability greater than or equal to 1 (i.e., a positive magnetic susceptibility) and hence are attracted to magnetic fields. For example, the paramagnetic susceptibility of the components of the mixture may be 0 emu, 0.1 emu (ie $1\times10^{-1}$ emu), 0.2 emu, 0.5 emu, 0.7 emu, 0.01 emu (ie $1\times10^{-2}$ emu), 0.02 emu, 0.05 emu, 0.07 emu, 0.001 emu (ie $1\times10^{-3}$ emu), 0.002 emu, 0.005 emu, 0.007 emu, or 0.0001 emu (ie $1\times10^{4}$ emu), or any value in between. As each different component of the mixture has a different diamagnetic susceptibility, no preferred values can be determined.

The weak magnetic field may be administered to the mixture by incorporating magnetic elements in a magnetic film as described above, into an applicator. Use of the applicator to spread the mixture over the skin then brings the mixture into the weak magnetic field generated by the magnetic film in the applicator.

The applicator containing the magnetic film that delivers the weak magnetic field may be moved over the surface of the skin or dermal barrier. The movement may be either through manual operation or through mechanical means. Where the movement is delivered through manual operation (ie through normal consumer actions such as rubbing or brushing) is used to mobilize the applicator device containing the magnetic film that delivers the weak magnetic field, the frequency will be in the order of 1 Hz to 5 Hz. In such cases, the strength of the magnet field produced by each element of the magnet array should be between about 1 mT and 100 mT. In the alternate, where movement is delivered through mechanical or electrical means (such as in the form of a roller ball driven or rotated by a motor) the oscillation should be in the order of approximately 100 and 8,000 Hz with a magnet flux of between about 1 mT and 100 mT.

The weak magnetic field works on the components of the mixture to destabilize the mixture through attracting some components towards the source of the weak magnetic field and pushing other components away from the source of the weak magnetic field. These contrary forces increase the energy within the mixture by creating internal opposing forces which work to decrease the stability of the emulsion, and assist in elevating the energy levels of the mixture beyond the transitional point, causing it to revert to its original separate lower energy multi-component parts.

Surface Energy

Preferably, the destabilizing energy form is provided in the form of surface energy. The term "surface energy" refers to the use of intermolecular forces (such as ion-dipole interactions (ion-dipole and ion-induced dipole forces); hydrogen bonding; dipole moments; Lennard-Jones potential; polarizability; and Van Der Waals interactions (Keesom [permanent-permanent dipoles] interactions; Debye [permanent-induced dipoles] forces; London dispersion forces)) from an external source to overcome the intermolecular forces within the mixture. Preferably the surface energy is provided by the use of materials of specific surface energy with known and desirable intermolecular forces to apply the mixture to the skin, wherein the surface energy of the material used to apply the mixture interacts with the components of the mixture to attract some components towards the material and repel some components of the mixture away from the material.

The surface energy provided by the material used to apply the mixture preferably has a surface energy of between 10-1,200 $mJ/m^2$. For example the surface energy may be 10 $mJ/m^2$, 18 $mJ/m^2$, 20 $mJ/m^2$, 30 $mJ/m^2$, 140 $mJ/m^2$, 50 $mJ/m^2$, 60 $mJ/m^2$, 70 $mJ/m^2$, 80 $mJ/m^2$, 90 $mJ/m^2$, 100 $mJ/m^2$, 120 $mJ/m^2$, 150 $mJ/m^2$, 170 $mJ/m^2$, 200 $mJ/m^2$, 220 mJ/m², 250 mJ/m², 270 mJ/m², 300 mJ/m², 320 mJ/m², 400 mJ/m², 500 mJ/m², 600 mJ/m², 700 mJ/m², 800 mJ/m², 900 mJ/m², 1,000 mJ/m², 1,100 mJ/m², 1,200 mJ/m² or any value in between. The surface energy may be in the range of 10-80 mJ/m², 10-100 mJ/m², 100-250 mJ/m², 250-500 mJ/m², 500-1,000 mJ/m², 1,000-1,200 mJ/m².

Preferably the surface energy is administered to the mixture through an applicator device. Through the choice of applicator device material, the present invention is able to target different types of components of the mixture. The surface energy may be administered to the mixture by incorporating materials with specific desired surface energy into the area of the applicator device that comes in contact with the skin. Use of the applicator device to spread the mixture over the skin then brings the mixture into contact with the surface energy generated by the materials in the applicator device.

TABLE 1

Surface energy of exemplary applicator device materials

| Material | Surface Energy (mJ/m²) |
|---|---|
| PTFE | 18-19 |
| Polypropylene | 30 |
| Poly(vinyl alcohol) PVA | 37 |
| Nylon | 46 |
| Poly(vinylchloride) PVC | 42 |
| Poly(ethylene terephthalate) PET | 45 |
| Poly (methyl methacrylate) PMMA | 33 |
| Glass | 250-500 |
| Copper | 1100-1350 |
| Nickel | 1770 |
| Platinum | 2672 |
| Silver | 890 |
| Aluminium | 800-1100 |

Typically, with some exceptions, materials with higher surface energies will repulse oil based components and lipophilic components and attract water based components and hydrophilic components. Also, with some exceptions, materials with lower surface energies will repel water based components and hydrophilic components and attract oil based components and lipophilic components.

Alternatively or in addition, materials that are hydrophilic will attract hydrophilic components and materials that are lipophilic will attract lipophilic components.

The applicator device containing the material that produces the surface energy may be moved over the surface of the skin or dermal barrier. The movement may be either through manual operation or through mechanical means. Where the movement is delivered through manual operation (ie through normal consumer actions such as rubbing or brushing of the surface with the applicator device), the frequency will be in the order of 1 Hz to 5 Hz. In such cases, the strength of the surface energy produced by the material should be between about 10-1,200 mJ/m³. In the alternate, where movement of the applicator device is delivered through mechanical or electrical means (such as in the form of a roller ball driven or rotated by a motor) the oscillation should be in the order of approximately 100 and 8,000 Hz with a surface energy of between about 10-1,200 mJ/m³.

The surface energy preferably works on the components of the mixture to attract some components towards the source of the surface energy and repel some components of the mixture away from the source of the surface energy. The surface energy increases the energy within the mixture by selectively attracting specific components of the mixture whilst repelling other components, and assists in elevating the energy levels of the mixture beyond the transitional point, causing it to revert to its original lower energy multi-component parts.

Thermal Energy

Preferably, the destabilizing energy form is provided in the form of thermal energy. The thermal energy is administered to the mixture in order to increase the temperature of the mixture.

The most desirable thermal energy will depend on the surface to which the mixture is applied. The thermal energy may be in the range of 20° C. to 100° C., more preferably 20° C. to 60° C., more preferably 20° C. to 40° C. For example, the thermal energy may be administered to the mixture by heating the mixture to 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 50° C., 60° C., 70° C., 80° C., 90° C., 100° C.

The thermal energy may be administered to the mixture by heating the mixture on the applicator device before application to the skin, or by applying the mixture to the skin, then heating it during application or spreading by a heated applicator device. The thermal energy may be administered to the mixture by incorporating a heating element into an applicator device. Use of the applicator device to spread the mixture over the skin then brings the mixture into the range of the thermal energy generated by the heating element in the applicator device.

The applicator device containing the heating element that produces the thermal energy may be moved over the surface of the skin or dermal barrier. The movement may be either through manual operation or through mechanical means. Where the movement of the applicator device is delivered through manual operation (ie through normal consumer actions such as rubbing or brushing), the frequency will be in the order of 1 Hz to 5 Hz. In such cases, the heating element should heat the mixture to between 20° C. and 40° C. In the alternate, where movement of the applicator device is delivered through mechanical or electrical means (such as in the form of a roller ball driven or rotated by a motor) the oscillation should be in the order of approximately 100 and 8,000 Hz and the heating element should heat the mixture to between 20° C. and 40° C.

The destabilizing energy form may be any combination of two or more of: a weak magnetic field, mechanical shear force, thermal energy and/or surface energy. The destabilizing energy form may be any combination of two destabilizing energy forms, three destabilizing energy forms or four destabilizing energy forms. Preferably, the destabilizing energy form is a combination of three destabilizing energy forms.

The combination of destabilizing energy forms may be chosen from the following:
 a weak magnetic field plus mechanical shear force
 a weak magnetic field plus thermal energy
 a weak magnetic field plus surface energy
 mechanical shear force plus thermal energy
 mechanical shear force plus surface energy
 thermal energy plus surface energy
 a weak magnetic field plus mechanical shear force plus surface energy
 a weak magnetic field plus mechanical shear force plus thermal energy
 a weak magnetic field plus surface energy plus thermal energy
 mechanical shear force plus thermal energy plus surface energy a weak magnetic field plus mechanical shear force plus surface energy plus thermal energy Preferably, the destabilizing energy form is a combination of a weak magnetic field plus mechanical shear force plus surface energy.

More preferably, the destabilizing energy form is a combination of mechanical shear force plus surface energy; thermal energy plus surface energy; or mechanical shear force plus thermal energy plus surface energy.

Preferably, the destabilizing energy form is a provided by a weak magnetic field of between 0.1 mT and 50 mT plus mechanical shear force applied at between about 150 Pa and 20,000 Pa plus surface energy of between 10-1,200 mJ/m². Preferably the mechanical shear force range is 400 Pa to 12,000 Pa.

More preferably, the destabilizing energy form is a provided by mechanical shear force applied at between about 150 Pa and 20,000 Pa plus thermal energy in the range of 20° C. to 40° C. plus surface energy of between 10-1,200 mJ/m². The destabilizing energy form may also be provided by mechanical shear force applied at between about 150 Pa and 20,000 Pa plus surface energy of between 10-1,200 mJ/m² or thermal energy in the range of 20° C. to 40° C. plus surface energy of between 10-1,200 mJ/m². Preferably the mechanical shear force range is 400 Pa to 12,000 Pa.

Energy Forms for Enriching

Preferably, the enriching energy form is used to form a first region that is enriched in a first component relative to the second component and a second region that is enriched in the second component relative to the first component.

Preferably, the enriching energy form interacts with a first component of the mixture to draw the component away from the skin to form a region that is enriched in the first component relative to a second component. The enriched region may be in the form of a spatial layer in proximity to the source of the enriching energy form.

Preferably, the enriching energy form interacts with a second component of the mixture to push the second component away from the enriching energy form towards the skin to form a region that is enriched in the second component relative to the first component. The enriched region may be in the form of a spatial layer in proximity to the skin.

It is preferred that the enriching energy form creates a concentration or lipophilicity gradient for the purposes of occlusion or barrier effect of one or more of the mixture components.

Even more preferably, the enriching energy form interacts concurrently with different components of the mixture to draw one or more components away from the skin to form a first spatial layer in proximity to the enriching energy form and at the same time interacts with one or more components of the mixture to push the component away from the enriching energy form towards the skin to form a second spatial layer in proximity to the skin.

Preferably, the destabilizing energy form is concurrently acting as an enriching energy form. Thus, as the destabilizing energy form is destabilizing a mixture by elevating the energy state of the mixture beyond its transitional point to overcome the intermolecular forces that hold the mixture in its stable state, it is also acting as an enriching energy form to form a first region that is enriched in a first component relative to the second component and a second region that is enriched in the second component relative to the first component.

It is preferred that the components being drawn towards the source of the enriching energy form are those of a more lipophilic nature. It is also preferred that the components being pushed towards the skin are of a more hydrophilic nature. However, the reverse (lipophilic to skin, hydrophilic to enriching energy form source) is also possible and may be desirable in some applications. Through the choice of strength and type of enriching form, the present invention is able to selectively draw away from the skin either the water or oil phase of the mixture.

Weak Magnetic Field

The enriching energy form may be provided as a weak magnetic field.

Preferably the weak magnetic field has the properties described above for the destabilizing energy form in the form of a weak magnetic field.

Preferably, the magnetic elements in the magnetic material that generates the weak magnetic field of the have the following parameters:

i) a horizontal off-set of between about 1 and 10 millimetres, 2 and 8 millimetres, or 3 and 7 millimetres; and/or
ii) a repetition rate of about 1 and 10 elements per centimetre, 1 and 6 elements per centimetre or 1.5 and 4 elements per centimetre; and/or
iii) the poles of the magnetic elements in a particular spatial region are between about 1.0 mm to 10 mm apart, or 1.0 mm to 5.0 mm apart; and/or
iv) the magnetic flux of each magnetic pole of the magnetic elements is between about 0.1 mT and 100 mT, 1 mT to about 60 mT, or 12 mT to 45 mT; and/or
v) the delta flux between the magnetic flux of two adjacent poles of opposite polarity is between about 0.2 mT and 200 mT, 20 mT to 140 mT, or 20 mT to 90 mT.

Preferably the magnetic material that generates the weak magnetic field is in the form of a magnetic film. Preferably the magnetic film is a flexible magnetic film. Preferably the magnetic film comprises magnetic elements, particles, fragments, or flakes disposed in a solid or semi-solid matrix, preferably a flexible solid or semi-solid matrix. Preferably the magnetic film used to generate an enriching energy form in the form of a weak magnetic field has the properties as described above for the magnetic film that generates the destabilizing energy form the form of a weak magnetic field.

The magnetic film may be present within the applicator device, in proximity to the area of the applicator device that comes in contact with the skin to spread the mixture over the skin. Alternatively, the material that forms the area of the applicator device that comes in contact with the skin may generate a weak magnetic field.

Preferably the weak magnetic field interacts with at least one first component of the mixture to induce paramagnetism and attraction of the first component towards the weak magnetic field. This attraction of a first component results in a region that is enriched in a first component of the destabilized mixture relative to a second component of the destabilized mixture, wherein the region is located proximate to the source of the enriching energy form.

The weak magnetic field may also interact with at least one second component of the mixture to induce diamagnetism and repulsion of the second component away from the weak magnetic field. This repulsion of a second component results in a region that is enriched in the second component of the destabilized mixture relative to the first component of the destabilized mixture, wherein the region is located proximate to the surface on which the mixture is applied.

Most preferably the weak magnetic field interacts with different components of the mixture to paramagnetically draw one or more first components away from the skin to form a spatial layer in proximity to the weak magnetic field that is enriched with the first components and at the same time interacts with one or more second components of the mixture to diamagnetically push the second component away from the weak magnetic field towards the skin to form a spatial layer in proximity to the skin that is enriched with the second components.

The utility of a weak magnetic field in the enrichment of different components of a mixture in different regions adjacent a skin surface and an applicator device can be increased not just by increasing the strength of an individual magnetic field, but also by taking advantage of the differences between the flux of two magnetic fields of alterative polarity and orientation. The dielectric polarized weak magnetic fields of the present invention are used to (i) diamagnetically repulse and/or paramagnetically attract components of a mixture to enrich different regions with different components; (ii) increase the permeability of target tissues and (iii) enhance diffusion of components of the mixture across dermal barriers in such a manner that one effect does not negative the benefit of another.

Most preferably, the weak magnetic field that is acting as the destabilizing energy form is concurrently acting as an enriching energy form. Thus, as the destabilizing energy form in the form of a weak magnetic field is destabilizing a mixture by elevating the energy state of the mixture beyond its transitional point to overcome the intermolecular forces that hold the mixture in its stable state, it is also acting as an enriching energy form to form a first region that is enriched in a first component relative to the second component and a second region that is enriched in the second component relative to the first component.

Surface Energy

Preferably the enriching energy form is surface energy.

Preferably the surface energy has the properties described above for the destabilizing energy form in the form of surface energy. Through the choice of material for the area of the applicator device that comes in contact with the skin, the present invention is able to target different types of components of the mixture.

The surface energy provided by the material that forms the area of the applicator device that comes in contact with the skin to apply the mixture preferably has an energy level of between 10-1,200 mJ/m$^2$.

The enriching energy form in the form of surface energy acts by the use of intermolecular forces (such as ion-dipole interactions (ion-dipole and ion-induced dipole forces); hydrogen bonding; dipole moments; Lennard-Jones potential; polarizability; and Van Der Waals interactions (Keesom [permanent-permanent dipoles] interactions; Debye [permanent-induced dipoles] forces; London dispersion forces)) from an external source to attract or repel different components of a mixture. Preferably the surface energy is provided by the use of specific materials with known and desirable intermolecular forces to apply the mixture to the skin, wherein the surface energy of the material used to apply the mixture interacts with the components of the mixture to attract some components towards the material and repel some components of the mixture away from the material.

Preferably the surface energy interacts with at least one first component of the mixture to draw the first component away from the skin towards the source of the surface energy to form a region that is enriched in the first component relative to a second component. The region enriched in the first component may be in the form of a spatial layer in proximity to the source of the surface energy.

The surface energy may also interact with at least one second component of the mixture to induce repulsion of the second component away from the source of the surface energy. This repulsion of a second component results in a region that is enriched in the second component of the destabilized mixture relative to the first component of the destabilized mixture, wherein the region is located proximate to the surface on which the mixture is applied.

Most preferably the surface energy interacts with different components of the mixture to draw the first component away from the skin towards the surface energy to form a region that is enriched in the first component relative to a second component and at the same time the surface energy is concurrently interacting with one or more second components of the mixture to push a second component away from the source of the surface energy towards the skin to form a spatial layer in proximity to the skin enriched in the second component.

Most preferably, the surface energy that is acting as the destabilizing energy form is concurrently acting as an enriching energy form. Thus, as the destabilizing energy form in the form of surface energy is destabilizing a mixture by elevating the energy state of the mixture beyond its transitional point to overcome the intermolecular forces that hold the mixture in its stable state, it is also acting as an enriching energy form to form a first region that is enriched in a first component relative to the second component and a second region that is enriched in the second component relative to the first component.

In an example of the present invention, one enriching energy form pushes a hydrophilic component of the mixture towards the skin, and another enriching energy form pulls a lipophilic component towards the source of the enriching energy forms. Thus there will be formed a region of increased hydrophilicity against the skin and a region of increased lipophilicity further away from the skin. The hydrophilic components are then located near the skin and the lipophilic components form an occlusive barrier between the region of increased hydrophilicity and the outside environment.

Alternatively, one enriching energy form may pull a hydrophilic component of the mixture towards the source of the enriching energy forms, and another enriching energy form may push a lipophilic component towards the skin. Thus there will be formed a region of increased hydrophilicity further away from the skin and a region of increased lipophilicity against the skin.

The enriching energy form may be a combination of two enriching energy form. The enriching energy forms may be a combination of a weak magnetic field plus surface energy.

Preferably, the enriching energy form is a provided by a weak magnetic field of between 0.1 mT and 50 mT plus surface energy of between 10-1,200 mJ/m$^2$.

More preferably the enriching energy form is a provided by surface energy of between 10-1,200 mJ/m$^2$.

There may be components of the mixture that are susceptible to both a weak magnetic field and surface energy. The direction of movement of these components (ie away from the applicator device or towards the applicator device) will depend on the relative strength of their susceptibility to the differing energy forms. For example, whilst a component may be diamagnetically repulsed by the weak magnetic field produced by a magnetic film within the area of the applicator device that comes in contact with the skin, if the area of the applicator device that comes in contact with the skin is made using a material with a surface force that attracts the component more strongly towards the surface of the applicator device than it is repulsed by the weak magnetic field, this surface force attraction will overcome the diamagnetic repulsion and the component will be enriched in a region nearer the applicator and away from the skin. Alternatively, the effect of the weak magnetic field and the surface force on the component may both be in the same direction. For example, the component may be both paramagnetically attracted to the weak magnetic field produced by a magnetic film within the area of the applicator device that comes in contact with the skin and attracted by the surface energy of the material that the area of the applicator device that comes in contact with the skin applicator is made from.

Undesirable Energy Forms

Some energy forms are not suitable to use in the method of the present invention, due to their tendency to alter or change the pharmacology, chemistry or function of the component or the skin during application. Such undesirable energy forms include electrical and micro-current forms, which are undesirable due to electro-migration of charged species altering the chemistry and concentration of the components within the mixture and has electroporation effects on skin barrier function. Electrical and micro-current forms cause disruption to ionic bonds and the current flow creates chemical changes within the mixture. Electrical and micro-current forms may also potentially cause damage to skin permeability. Ultra-sound or sonophoresis is also undesirable due to their effects on the skin barrier such as potentially damaging cavitations and lipid fluidization.

Strong magnetic fields, such as those with a field strength of 5,000-50,000 Gauss or more are also not suitable for use in the present invention, as they increase the entropic motion of the components of the mixture. This increase in the randomness of the motion of the components results in the components not moving in the specific directions desired.

Heating the mixture, and the skin if that is where the mixture is to be applied, to too high a temperature may also be undesirable. Too great a temperature is destructive to many cosmetic and therapeutic components of mixtures, and is potentially damaging to the skin's delicate barrier functions. Temperatures beyond about 50° C. also not suitable for use in the present invention if the mixture is being applied to skin.

Preferably the mixture applied to the skin surface contains at least one component that is subject to an enriching energy form as described above.

The initial energy level of the mixture will be influenced by the nature of the components of the mixture. Mixtures with higher intermolecular forces will respond better to the method and device of the present invention. For example, mixtures with higher intermolecular forces will respond better to the destabilizing energy forms of the present invention. Furthermore, mixtures made up of components with higher intermolecular forces will respond better to enriching energy forms of the present invention.

Preferably, the mixture contains at least one component that is subject to an enriching energy form that pushes that component towards the skin, away from the enriching energy source. Preferably the mixture contains at least one component that is subject to an enriching energy form that pulls that component towards the enriching energy source, away from the skin.

For example, many organic components are subject to diamagnetic repulsion, and are moved away from the enriching energy form in the form of a weak magnetic field, and moved towards the skin. Thus components that are organic may be moved into a spatial region closer to the skin and be enriched in this region.

However, it is possible to divide even organic components into different spatial regions by applying two different enriching energy forms. Even if some organic components are moved towards the skin through the use of a weak magnetic field and diamagnetic repulsion, if a second enriching energy source is applied to the mixture that pulls at least one organic component towards the enriching energy source with a strength that overcomes the diamagnetic repulsion, then a region will form close to the skin that contains some organic components of the mixture (those subject more strongly to the diamagnetic push), and another region will form close to the enriching energy form that contains at least one other component of the mixture that is subject more strongly to an enriching energy form that pulls the component more strongly than the diamagnetic repulsion pushes.

An example of the use of two different enriching energy forms may be the use of a weak magnetic field to diamagnetically repulse one component away from the enriching energy forms; in conjunction with surface energy to attract another component towards the source of the enriching energy forms. For example, the diamagnetic repulsion may preferably push a hydrophilic component such as niacinamide towards the skin, and the surface energy may preferably pull a lipophilic component such as paraffin towards the source of the enriching energy forms. Thus there will be formed a region of increased hydrophilicity against the skin and a region of increased lipophilicity further away from the skin and nearer the source of the enriching energy forms. The hydrophilic components are then able to move into the skin and the lipophilic components form an occlusive barrier between the region of increased hydrophilicity and the outside environment.

Alternatively, diamagnetic repulsion may be used to push a lipophilic component such as retinol towards the skin to form a region near the skin that is enriched in this component, whilst concurrently the surface energy may pull a hydrophilic component such as water towards the source of the enriching energy forms to form a region that has reduced amounts of the component.

The mixture may be in the form of creams, ointments, liniments (balms), pastes, films or liquids. The different mixture forms are often a function of their oil-to-water ratios and/or other additives and excipients in the formulation.

Topical dosage forms of the mixture may be used on the surface of the skin, transdermally, transmucosally, ophthalmically, rectally, or vaginally.

If the mixture is in the form of an emulsion, the emulsion may be water-in-oil (w/o), oil-in-water (o/w), water-in-oil-in-water (w/o/w) or oil-in-water-in-oil (o/w/o), or biocontinuous emulsion. The particle size of the emulsion may form a traditional macroemulsion (eg droplet sizes of about 10-1000 μm), a microemulsion (eg droplet sizes of about 1-10 μm), or a nanoemulsion (eg droplet sizes of 0.01-1 μm), or any other type of emulsion known to the skilled reader.

The mixture employed in the present invention may include additives such as other buffers, diluents, carriers, adjuvants or excipients. Any pharmacologically acceptable buffer that is magnetically inert or neutral; or which has a magnetic susceptibility that is either paramagnetic in nature or is more paramagnetic than the components being delivered to the surface of the skin, may be used. For example tris buffers or phosphate buffers.

Other excipients may be employed in the mixture for a variety of purposes. For example, buffering agents, preservatives, co-solvents, surfactants, oils, humectants, emollients, chelating agents, stabilizers or antioxidants may be employed. Preservatives which may be employed include, but are not limited to: benzalkonium chloride, chlorobutanol, thimerosal, sodium bisulfate, phenylmercuric acetate, phenylmercuric nitrate, ethyl alcohol, methylparaben, polyvinyl alcohol, benzyl alcohol, germaben, parabens, imidureas, kathon and phenylethyl alcohol. The mixture may further comprise a surfactant such as Tween 80. Other components of the mixture may include, but are not limited to, polyvinyl alcohol, povidone, hydroxypropyl methyl cellulose, poloxamers, carboxymethyl cellulose, hydroxyethyl cellulose, purified water, etc. Tonicity adjustors and electrolytes such as, for example, sodium chloride, potassium chloride, mannitol, glycerin, etc may also be included. Antioxidants include, but are not limited to, sodium metabisulfite, sodium thiosulfate, acetylcysteine, butylated hydroxyanisole, butylated hydroxytoluene, etc.

Suitable buffering agents that may be employed in the mixture may include sodium carbonate, sodium borate, sodium phosphate, sodium acetate, sodium bicarbonate, etc., as approved by the US FDA for the desired route of administration. These agents may be present in amounts sufficient to maintain a pH of the system of between about 2 to about 9, preferably about 4 to about 8, more preferably 4.5, 5, 5.5, 6, 6.5, 7 or 7.5 (or any pH in between). As such the buffering agent may be as much as about 5% on a weight to weight basis of the total composition.

The mixture may also comprise solvents such as propylene glycol, water and ethanol; preservatives such as germaben; viscosity modifying agents such as gelatine; vitamins such as vitamin C and E. The mixture may further comprise additives such as colouring agents and/or perfuming agents such as essential oils, esters etc.

The indications, effective doses, contra-indications, vendors etc, of the components being delivered to the skin surface are available or are known to one skilled in the art.

The present invention further provides an applicator device for the separation of a mixture having a first component and a second component, said applicator device comprising:
a) means to generate at least two destabilizing energy forms chosen from the list comprising: a weak magnetic field, mechanical shear force, thermal energy, and/or surface energy;
b) a means to generate at least one enriching energy form chosen from the list comprising: a weak magnetic force, surface energy wherein during use the destabilizing energy forms destabilize the mixture and the enriching energy form forms a first region that is enriched in the first component relative to the second component and a second region that is enriched in the second component relative to the first component.

Preferably the applicator device for destabilization of a mixture comprises means for generating at least two destabilizing energy forms and means for generating at least two enriching energy forms.

More preferably the applicator device for destabilization of a mixture comprises (i) means for generating at least two destabilizing energy forms; and (ii) means for generating surface energy as the enriching energy form.

More preferably the applicator device for destabilization of a mixture comprises (i) means for generating at least two destabilizing energy forms wherein one of destabilizing energy forms is surface energy; and (ii) means for generating surface energy as the enriching energy form.

Preferably the mixture is applied to a surface, more preferably a skin surface, before the applicator is used to carry out separation.

At least one of the destabilizingdestabilizing energy forms is preferably concurrently acting as an enriching energy form. Thus, as the destabilizing energy form is destabilizing a mixture by elevating the energy state of the mixture beyond its transitional point to overcome the intermolecular forces that hold the mixture in its stable state, it is also acting as an enriching energy form to form a first region that is enriched in a first component relative to the second component and a second region that is enriched in the second component relative to the first component.

Preferably the destabilizing energy forms provided by the device to destabilise the mixture are sufficient to overcome the intermolecular forces within the mixture. The destabilizing energy forms elevate the energy state of the mixture beyond its transitional point, thus overcome the intermolecular forces that hold the mixture in its stable state. This then causes the mixture to return to its original separate multi-component form without altering the chemical structure, pharmacology or function of the individual components.

Preferably the destabilizing energy forms provided by the applicator device are any combination of two or more of: a weak magnetic field, mechanical shear force, thermal energy and/or surface energy. The destabilizing energy form may be any combination of two destabilizing energy forms, three destabilizing energy forms or four destabilizing energy forms. Preferably, the destabilizing energy form is a combination of three destabilizing energy forms. Preferably the weak magnetic field, mechanical shear force, thermal energy and surface energy produced by the device have the properties described above for the weak magnetic field, mechanical shear force, thermal energy and surface energy used as a destabilizing energy.

Preferably, the enriching energy form provided by the applicator device forms a first region that is enriched in the first component relative to the second component and a second region that is enriched in the second component relative to the first component. The enriched regions may be in the form of spatial layers, the first in proximity to the source of the enriching energy form and the second in proximity to the skin.

Preferably, the enriching energy form provided by the applicator device is a weak magnetic field and/or surface energy. Preferably the weak magnetic field and surface energy have the properties described above for the weak magnetic field and the surface energy used as a destabilizing energy.

Preferably, the applicator device is producing both a destabilizing energy form and an enriching energy form. Preferably, the destabilizing energy form produced by the device is concurrently acting as an enriching energy form. Thus, as the destabilizing energy form is destabilizing a mixture by elevating the energy state of the mixture beyond its transitional point to overcome the intermolecular forces that hold the mixture in its stable state, it is also acting as an enriching energy form to form a first region that is enriched in a first component relative to the second component and a second region that is enriched in the second component relative to the first component.

Preferably, the destabilizing energy forms produced by the applicator device are a combination of a weak magnetic field plus mechanical shear force plus surface energy. More preferably, the destabilizing energy form is a combination of mechanical shear force plus surface energy; thermal energy plus surface energy; or mechanical shear force plus thermal energy plus surface energy.

Preferably, the destabilizing energy forms produced by the applicator device are a weak magnetic field of between 0.1 mT and 50 mT plus mechanical shear force applied at between about 150 Pa and 20,000 Pa plus surface energy of between 10-1,200 mJ/m². Preferably the mechanical shear force range is 400 Pa to 12,000 Pa The enriching energy forms produced by the applicator device may be a combination of two enriching energy form. The enriching energy forms may be a combination of a weak magnetic field plus surface energy.

Preferably, the enriching energy form forms produced by the applicator device are a weak magnetic field of between 0.1 mT and 50 mT plus surface energy of between 10-1,200 mJ/m². More preferably the enriching energy form is a provided by surface energy of between 10-1,200 mJ/m².

The applicator device comprising means to generate at least two destabilizing energy forms and a means to generate at least one enriching energy form is used to apply a mixture on the dermal surface or skin. Preferably the applicator device is in the form of an applicator device. The mixture may be applied to the skin, and then spread over the skin using the applicator device, or the mixture may be applied to the applicator device and then the applicator device with the mixture on it may be applied to the skin to spread the mixture. The applicator device can be moved or rubbed, either manually or by motorised action over the dermal surface.

Examples of applicator devices include roller balls; pads such as fabric pads or sponges; solid surface applicators such as sticks, wands, paddles etc.

The applicator device contains means to generate the destabilizing energy forms and means to generate the enriching energy forms of the present invention. For example, the materials that form the area of the applicator device that come in contact with the skin may be chosen such that they generate a destabilizing energy form and/or an enriching energy form (for example a material with a specific surface force or a material that generates a weak magnetic field). In addition or alternatively, the applicator device may contain a means to generate a destabilizing energy form and/or an enriching energy form (for example a magnetic film as described above, or a heating element) that is located adjacent the area of the applicator device that comes in contact with the skin.

The applicator device that applies the mixture may be moved over the surface of the skin or dermal barrier. The movement may be either through manual operation or through mechanical means. Where movement of the applicator device is delivered through manual operation (ie through normal consumer actions such as rubbing or brushing), the frequency will be in the order of 1 Hz to 5 Hz. In the alternate, where movement is delivered through mechanical or electrical means (such as in the form of a roller ball driven or rotated by a motor) the oscillation should be in the order of approximately 100 and 8,000 Hz. If the movement is delivered through mechanical or electrical means, the applicator device preferably includes a means for moving at least a portion of the applicator over the dermal barrier. That portion of the applicator device should be at least the area of the applicator device that comes in contact with the skin. Such a means will include any mechanism, electronic or mechanical, adapted for reciprocal or rotational movement of at least a portion of the applicator. For example, the applicator may contain a drive mechanism that is capable of reciprocal movement, preferably reciprocal movement of the area of the applicator device that comes in contact with the skin.

As used herein, rotational includes movement in an arc-like, semi-circular, circular or orbital manner.

An example of a device in accordance with the present invention is roller-ball applicator. The ball of the roller ball applicator contains a magnetic film that generates a weak magnetic field (<500 Gauss). The ball is made of aluminium, which has high surface energy (about 1,000 $mJ/m^2$).

As the roller ball applicator is moved across the skin to apply a thin film of a mixture to the skin, the following effects will occur simultaneously:

i) shear forces will be created in the mixture;

ii) the weak magnetic field will cause repulsion of those components of the mixture with high diamagnetic susceptibility, particularly the organic components of the mixture; and iii) the aluminium roll-ball with high surface energy (>1,000 $mJ/m^2$) will create strong attraction forces between itself and the aqueous phase of the formulation.

The shear force and repulsion and attraction of different components caused by the effect of the weak magnetic field and the surface energy will combine to elevate molecule energy levels within the mixture until they overcome the formulation's intermolecular forces, tipping it over its transitional point and allowing the mixture to revert to its separate constituent components. As the mixture is transitioning to its basic components, the diamagnetic repulsion will push those components with diamagnetic susceptibility away from the magnetic film within the roller ball device and towards the skin. Simultaneously, the surface energy of the roller ball will attract the aqueous phase towards the roller ball and away from the skin. The result will be a predictable enrichment of the mixture's components in proximity to the skin and in proximity to the roller ball applicator.

General

Those skilled in the art will appreciate that the invention described herein is susceptible to variations and modifications other than those specifically described. It is to be understood that the invention includes all such variations and modifications. The invention also includes all of the steps, features, mixtures and components referred to or indicated in the specification, individually or collectively and any and all combinations or any two or more of the steps or features.

The present invention is not to be limited in scope by the specific embodiments described herein, which are intended for the purpose of exemplification only. Functionally equivalent devices, mixtures, components and methods are clearly within the scope of the invention as described herein.

The entire disclosures of all publications (including patents, patent applications, journal articles, laboratory manuals, books, or other documents) cited herein are hereby incorporated by reference. No admission is made that any of the references constitute prior art or are part of the common general knowledge of those working in the field to which this invention relates.

Each document, reference, patent application or patent cited in this text is expressly incorporated herein in their entirety by reference, which means that it should be read and considered by the reader as part of this text. That the document, reference, patent application or patent cited in this text is not repeated in this text is merely for reasons of conciseness.

Any manufacturer's instructions, descriptions, product specifications, and product sheets for any products mentioned herein or in any document incorporated by reference herein, are hereby incorporated herein by reference, and may be employed in the practice of the invention.

As used herein the term "derived" and "derived from" shall be taken to indicate that a specific integer may be obtained from a particular source albeit not necessarily directly from that source.

As used herein, the singular forms "a," "an" and "the" include plural references unless the context clearly dictates otherwise.

Throughout this specification, unless the context requires otherwise, the word "comprise", or variations such as "comprises" or "comprising", will be understood to imply the inclusion of a stated integer or group of integers but not the exclusion of any other integer or group of integers.

Other than in the operating example, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the specification and claims are approximations that may vary depending upon the desired properties sought to be obtained by the present invention. Hence "about 80%" means "about 80%" and also "80%". At the very least, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value; however, inherently contains certain errors necessarily resulting from the standard deviation found in their respective testing measurements Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

The following examples serve to more fully describe the manner of using the above-described invention, as well as to set forth the best modes contemplated for carrying out various aspects of the invention. It is understood that these methods in no way serve to limit the true scope of this invention, but rather are presented for illustrative purposes.

EXAMPLES

Further features of the present invention are more fully described in the following non-limiting Examples. This description is included solely for the purposes of exemplifying the present invention. It should not be understood as a restriction on the broad description of the invention as set out above.

Example 1

Use of Surface Free Energy to Separate a Mixture

The subject's volar forearm or upper arm was delineated into two 3×3 cm square regions which were designated Nylon and Polypropylene. An aliquot of a standard Aqueous B.P. cream containing 5% Vitamin E mixture or standard Aqueous B.P. cream containing 5% niacinamide was applied to both regions and then rubbed into the skin surface with the appropriate applicator. After an absorption period of 30 minutes, the excess mixture was removed from each region by washing with water. The region was then tape stripped using the adapted procedure of Lademann et al (*The tape stripping procedure—evaluation of some critical parameters*. European Journal of Pharmaceutics and Biopharmaceutics 72 (2009) 317-323).

The tape strip samples were then analysed for Vitamin E or niacinamide using a validated HPLC method.

TABLE 2

Vitamin E penetration when applied with a Nylon applicator
Nylon

| Tape Strip | Average |
| --- | --- |
| 1 | 21.14277207 |
| 2 | 4.940799679 |
| 3 | 3.139052324 |
| 4 | 2.561392867 |
| 5 | 2.190040359 |
| 6 | 1.681149885 |
| 7 | 1.37856636 |
| 8 | 1.268535987 |
| 9 | 0.800906902 |
| 10 | 0.663368936 |
| Total (2-10) | 18.6238133 |

TABLE 3

Vitamin E penetration when applied with a Polypropylene applicator
Polypropylene

| Tape Strip | Average |
| --- | --- |
| 1 | 6.522486288 |
| 2 | 4.706985137 |
| 3 | 2.341332122 |
| 4 | 2.368839715 |
| 5 | 1.804934054 |
| 6 | 1.639888495 |
| 7 | 1.075982834 |
| 8 | 0.800906902 |
| 9 | 0.732137919 |
| 10 | 0.56709236 |
| Total (2-10) | 16.03809954 |

TABLE 4

Niacinamide penetration when applied with a Nylon applicator
Nylon

| Tape Strip | Average |
| --- | --- |
| 1 | 4.479341128 |
| 2 | 3.156535433 |
| 3 | 2.824877555 |
| 4 | 2.41521118 |
| 5 | 1.860027052 |
| 6 | 1.421335406 |
| 7 | 1.103066217 |
| 8 | 1.334681039 |
| 9 | 0.921278335 |
| 10 | 0.849739861 |
| Total (2-10) | 15.88675208 |

TABLE 5

Niacinamide penetration when applied with a Polypropylene applicator
Polypropylene

| Tape Strip | Average |
|---|---|
| 1 | 4.498794321 |
| 2 | 3.240007109 |
| 3 | 3.592246269 |
| 4 | 2.691329525 |
| 5 | 1.972152915 |
| 6 | 1.405191501 |
| 7 | 1.25788787 |
| 8 | 1.239996941 |
| 9 | 1.168187673 |
| 10 | 1.013962798 |
| Total (2-10) | 17.5809626 |

It can be seen that use of a nylon applicator resulted in much greater penetration of the Vitamin E (FIG. 2) into the skin than use of a polypropylene applicator. Nylon is a hydrophilic material and attracts hydrophilic components such as water. This results in the nylon of the applicator acting on the Vitamin E mixture to destabilise the mixture and draw the aqueous components of the mixture towards to applicator, leaving a higher concentration of Vitamin E (a lipophilic substance) near the skin. This encourages increased penetration by the Vitamin E due to the concentration gradient generated. In contrast, polypropylene is a lipophilic material, and its use as an applicator results in the attraction of lipophilic components such as Vitamin E. As the lipophilic components are at in a higher concentration away from the skin, nearer to the applicator, the penetration of the Vitamin E component is reduced.

In contrast, niacinamide is a hydrophilic component. Therefore, use of a hydrophilic nylon applicator reduces the amount of niacinamide next to the skin by attracting the component away from the surface and towards the applicator. The reduced concentration results in a reduced penetration of niacinamide into the skin. When a lipophilic applicator is used, the lipophilic components are attracted towards the applicator, leaving an increased concentration of niacinamide near the skin resulting in increased penetration due to the concentration gradient.

Example 2

Use of a Weak Magnetic Field to Separate a Mixture
Procedure: Gel Mixture

| | % | Amount |
|---|---|---|
| Ultrez 20 | 3.731 | 0.280 g |
| Manganese Carbonate | 0.466 | 0.035 g |
| Niacinamide | 1.865 | 0.140 g |
| Isopropyl Alcohol | 13.324 | 1 mL |
| Milli-Q Water | 80.613 | 6.05 mL |
| Total | 100 | 7.505 | i) Dissolve niacinamide (0.140 g) in 6.05 mL Milli-Q water
ii) Heat solution in microwave for 8 seconds
iii) Vortex briefly, leave on magnetic stirrer
iv) Slowly add Ultrez 20 (0.280 g), vortex occasionally to help with the incorporation of Ultrez 20 into the solution
v) Add 500 μL of isopropyl alcohol to the thick clear gel
vi) Add manganese carbonate (0.035 g) to the gel
vii) Leave spinning on the magnetic stirrer for 5 days ($MnCO_3$ slowly dissolves into gel)
viii) Add the remaining 500 μL of isopropyl alcohol and vortex vigorously Weak Magnetic Field ETP008—a linear array of displaced dipolar magnetic elements comprising strontium oxides dispersed in a PVC film base. The displaced dipolar magnetic elements were created in parallel with a pole flux of 450 Gauss. Each element or pole was 2.7 mm wide, creating a pair of displaced dipolar magnetic elements of pitch of 1.5 pairs per centimetre. Inter-pair flux gradient was 900 Gauss or 1350 Gauss per centimetre.

Procedure: Tape Stripping

The subject's volar forearm or upper arm was delineated into two 2.5 cm diameter regions which were designated Passive (no weak magnetic field) and Active (weak magnetic field generated by ETP008). An aliquot of the niacinamide mixture was applied to both regions without rubbing. A magnetic film (ETP008) was placed in close proximity (approximately 0.5 mm) above the Active region for 5 minutes. After an absorption period of 30 minutes, the excess mixture was removed from each region by washing with water and then tape stripped using the adapted procedure of Lademann et al (*The tape stripping procedure—evaluation of some critical parameters.* European Journal of Pharmaceutics and Biopharmaceutics 72 (2009) 317-323).

The Tape strip samples were then analysed for niacinamide using a validated mass spectrometry method.

TABLE 6

Niacinamide penetration when applied with a Passive applicator
Passive

| Tape Strip | 1 | 2 | 3 | 4 | 5 | 6 | Average | STDEV | SEM |
|---|---|---|---|---|---|---|---|---|---|
| 1 | 4.785242 | 1.996572 | 0.806842 | 3.160351 | 2.0563 | 1.760699 | 2.427668 | 1.377727 | 0.562455 |
| 2 | 1.077287 | 0.977819 | 1.464385 | 0.984214 | 1.846272 | 1.767723 | 1.35295 | 0.395095 | 0.161297 |
| 3 | 0.607107 | 0.816588 | 1.131057 | 1.06009 | 1.456277 | 2.084624 | 1.192624 | 0.523596 | 0.213757 |
| 4 | 0.4947 | 1.296906 | 0.895358 | 0.545606 | 0.840573 | 1.688854 | 0.960333 | 0.458563 | 0.187208 |
| 5 | 0.592498 | 0.851571 | 0.934989 | 0.665536 | 0.621332 | 1.303321 | 0.828208 | 0.269258 | 0.109924 |
| 6 | 0.573606 | 0.575894 | 0.725827 | 0.543209 | 0.638524 | 0.648678 | 0.617623 | 0.066822 | 0.02728 |
| 7 | 0.593583 | 0.486747 | 0.50564 | 0.622044 | 0.546724 | 0.91269 | 0.611238 | 0.156277 | 0.0638 |
| 8 | 0.565697 | 0.400634 | 0.43131 | 0.363364 | 0.487784 | 0.5195 | 0.461382 | 0.076365 | 0.031176 |

TABLE 6-continued

| | Niacinamide penetration when applied with a Passive applicator | | | | | | | | |
|---|---|---|---|---|---|---|---|---|---|
| | Passive | | | | | | | | |
| Tape Strip | 1 | 2 | 3 | 4 | 5 | 6 | Average | STDEV | SEM |
| 9 | 0.314578 | 0.404773 | 0.416829 | 0.424819 | 0.242232 | 0.395383 | 0.366435 | 0.072624 | 0.029649 |
| 10 | 0.35631 | 0.521538 | 0.210693 | 0.444242 | 0.318627 | 0.528309 | 0.39662 | 0.124492 | 0.050824 |
| Total (6-10) | 2.403774 | 2.389585 | 2.290298 | 2.397677 | 2.233891 | 3.00456 | 2.453298 | 0.278641 | 0.113755 |

TABLE 7

| | Niacinamide penetration when applied in the presence of a Weak Magnetic Field applicator | | | | | | | | |
|---|---|---|---|---|---|---|---|---|---|
| | Active | | | | | | | | |
| Tape Strip | 1 | 2 | 3 | 4 | 5 | 6 | Average | STDEV | SEM |
| 1 | 4.463088 | 1.098619 | 1.021081 | 3.470247 | 2.739385 | 4.646805 | 2.906537 | 1.588748 | 0.648604 |
| 2 | 1.782059 | 0.564913 | 1.06971 | 1.211143 | 2.226163 | 5.363796 | 2.036297 | 1.72934 | 0.706 |
| 3 | 1.136643 | 0.514653 | 1.116268 | 1.035128 | 1.693945 | 1.226149 | 1.120464 | 0.378052 | 0.154339 |
| 4 | 0.988768 | 0.708674 | 1.097992 | 0.854807 | 0.842514 | 0.784753 | 0.879585 | 0.14129 | 0.057681 |
| 5 | 0.914609 | 0.781441 | 0.749494 | 0.880781 | 1.166825 | 0.640209 | 0.85556 | 0.181178 | 0.073966 |
| 6 | 0.895021 | 0.814516 | 0.528723 | 0.875693 | 0.753091 | 0.677698 | 0.757457 | 0.137738 | 0.056231 |
| 7 | 0.626134 | 0.550195 | 0.485944 | 0.632052 | 0.660799 | 1.049302 | 0.667404 | 0.197741 | 0.080728 |
| 8 | 0.414931 | 0.710708 | 0.474139 | 0.554143 | 0.575318 | 0.673925 | 0.567194 | 0.113197 | 0.046212 |
| 9 | 0.466595 | 0.539559 | 0.405863 | 0.462733 | 0.489837 | 0.298549 | 0.443856 | 0.083312 | 0.034012 |
| 10 | 0.422923 | 0.398226 | 0.380854 | 0.233643 | 0.518711 | 0.324273 | 0.379772 | 0.095856 | 0.039133 |
| Total (6-10) | 2.825604 | 3.013203 | 2.275522 | 2.758264 | 2.997756 | 3.023748 | 2.815683 | 0.286574 | 0.116994 |

The presence of the weak magnetic field resulted in destabilization of the mixture and in situ formation of layers by drawing away from the skin towards the weak magnetic field those components that are paramagnetic and pushing those components of the skin that have diamagnetic properties. The niacinamide is pushed towards the skin by the presence of the weak magnetic field as it has diamagnetic properties. The enrichment of components through their diamagnetic/paramagnetic properties further results in increased concentrations of lipophilic components near the source of the weak magnetic field and production of an occlusive lipophilic region above the hydrophilic region that is next to the skin.

Example 3

Use of Mechanical Shear Force to Separate a Mixture
Application Method:

9.4 mg of a standard Aqueous B.P. cosmetic cream containing 5% Niacinamide was applied to the inner forearm of subject in three 3 cm×6 cm rectangles. A chrome applicator, calibrated to pressures 19174 Pa, 11465 Pa and 582 Pa, was used to rub in the cream for 30 seconds, with one pressure per rectangle. After 30 minutes the subject washed the area with soapy water and dried the area.

Figure 5:
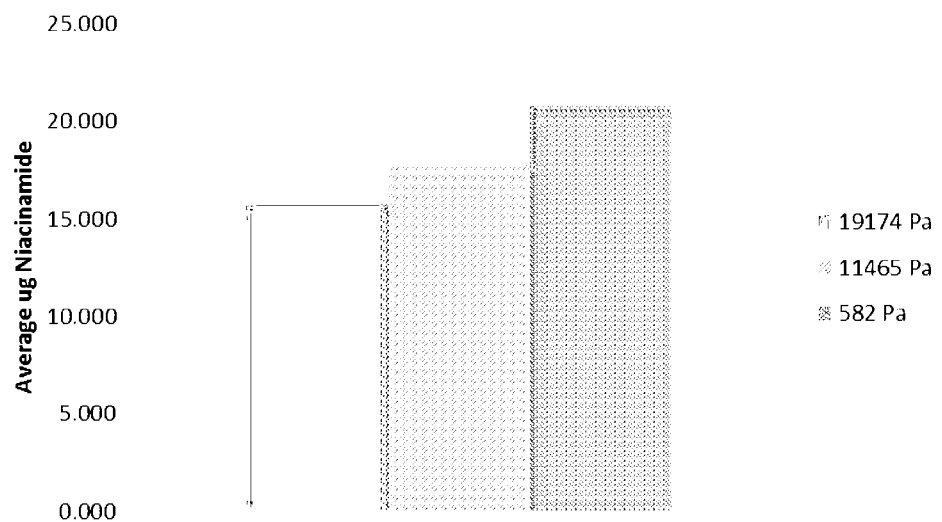

The skin in each of the application rectangles was the tape stripped to determine the content of Niacinamide directly under each of the treatment areas. FIG. 5 shows that a pressure of 582 Pa provided best results.

TABLE 8

| Niacinamide penetration when applied in the presence of Mechanical Shear Force | | | |
|---|---|---|---|
| | 1 | 2 | 3 |
| 19174 Pa | 10.85608 | 22.54464 | 13.94167 |
| 11465 Pa | 13.62824 | 24.10491 | 15.6611 |
| 582 Pa | 14.83133 | 25.20333 | 22.53046 |

Example 4

Use of Pressure Plus Surface Energy to Separate a Mixture
Application Method:

18.8 mg of a standard Aqueous B.P. cosmetic cream containing 5% Niacinamide was applied to the inner forearm of subject in four 3 cm×6 cm rectangles. A polypropylene applicator calibrated to pressures 19174 Pa, 11465 Pa and 582 Pa was used to rub in the cream for 30 seconds, with one pressure per rectangle. A further chrome applicator calibrated to pressures 582 Pa was used to rub in the cream for 30 seconds on the fourth rectangle. After 30 minutes the subject washed the area with soapy water and dried the area.

Figure 6:
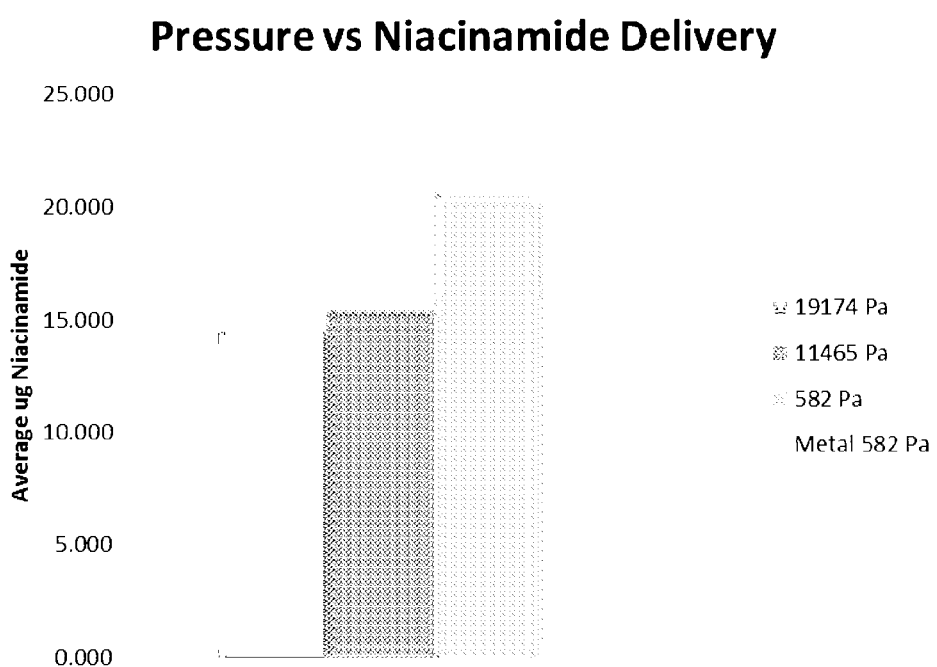

The skin was the tape stripped to determine the content of Niacinamide directly under each of the treatment areas. FIG. 6 shows that a pressure of 582 Pa and a polypropylene applicator provided best results, better than a chrome applicator.

TABLE 9

Niacinamide penetration when applied in the presence
of Mechanical Shear Force and Surface Energy

| | Average Niacinamide |
|---|---|
| 19174 Pa | 14.486 |
| 11465 Pa | 15.4785 |
| 582 Pa | 20.6872 |
| Metal 582 Pa | 16.2853 |

The results show that a polypropylene applicator at 582 Pa is more effective at ensuring penetration of water soluble components of the cosmetic mixture into the skin than a chrome applicator at 582 Pa. This is because the polypropylene applicator has a lower surface energy than the metal applicator. Therefore, the polypropylene applicator is repelling water based components and hydrophilic components (niacinamide) and pushing them into the skin and attracting oil based components and lipophilic components to form an occlusive surface much more strongly than the metal applicator.

Numerous variations and modifications of the above-described modes of carrying out the various embodiments of this invention will be apparent to those skilled in the art, based on the above teachings related to the disclosed invention, without departing from the basic inventive concepts. The above embodiments of the invention are merely exemplary and should not be construed to be in any way limiting and all such variations and modifications are to be considered within the scope of the present invention, the nature of which is to be determined from the foregoing description.

The invention claimed is:

1. A method for the in situ separation of a mixture on a dermal surface, said mixture having a first lipophilic component and a second hydrophilic component, the method comprising the steps of:
    a) applying at least two destabilizing energy forms to the mixture to destabilize the mixture, wherein at least one of the destabilizing energy forms is a surface energy destabilizing energy form generated by a first material that (i) generates a surface energy at between 1,000-1,200 mJ/m$^2$ and (ii) is capable of producing the second destabilizing energy form as mechanical shear force at between 400-12,000 Pa; and
    b) applying at least one enriching energy form to the mixture to form a first region that is enriched in the first component relative to the second component and a second region that is enriched in the second component relative to the first component, wherein the enriching energy form is a surface energy enriching energy form generated by a second material that generates a surface energy at between 10-100 mJ/m$^2$.

2. An applicator device for the in situ separation of a mixture on a dermal surface, said mixture having a first lipophilic component and a second hydrophilic component, said device comprising:
    a) a means to generate at least two destabilizing energy forms wherein the first destabilizing energy form is a surface energy destabilizing energy form, and wherein the surface energy destabilizing energy form is generated by a first material that (i) generates a surface energy at between 1,000-1,200 mJ/m$^2$ and (ii) is capable of producing the second destabilizing energy form as mechanical shear force at between 400-12,000 Pa; and
    b) a means to generate at least one enriching energy form that is a surface energy enriching energy form, wherein the surface energy enriching energy form is generated by a second material that generates a surface energy at between 10-100 mJ/m$^2$, and
    c) a surface of the applicator device to contact the dermal surface,
    wherein the means for generating the destabilizing energy forms of part (a) and the surface energy enriching energy form of part (b) are the materials that form at the surface of the applicator device of part (c), and
    wherein during use the destabilizing energy form destabilizes the mixture and the enriching energy form forms a first region that is enriched in the first component of the destabilized mixture relative to the second component of the destabilized mixture and a second region that is enriched in the second component relative to the first component.

3. The method of claim 1, wherein the mixture is applied to the dermal surface using an applicator device for the in situ separation of a mixture on a surface, said device comprising:
    a) a means to generate at least two destabilizing energy forms wherein the first destabilizing energy form is a surface energy destabilizing energy form, and wherein the surface energy destabilizing energy form is generated by a first material that (i) generates a surface energy at between 1,000-1,200 mJ/m$^2$ and (ii) is capable of producing the second destabilizing energy form as mechanical shear force at between 400-12,000 Pa; and
    b) a means to generate at least one enriching energy form that is a surface energy enriching energy form and wherein the surface energy enriching energy form is generated by a second material that generates a surface energy at between 10-100 mJ/m$^2$,
    c) a surface of the applicator device to contact the dermal surface,
    wherein the means for generating the destabilizing energy forms of part (a) and the surface energy enriching energy form of part (b) are the materials that form at the surface of the applicator device of part (c), and
    wherein during use the destabilizing energy form destabilizes the mixture and the enriching energy form forms a first region that is enriched in the first component of the destabilized mixture relative to the second component of the destabilized mixture and a second region that is enriched in the second component relative to the first component.

4. The method of claim 1, wherein
    the first region that is enriched in a first lipophilic component of the destabilized mixture relative to the second hydrophilic component of the destabilized mixture is located proximate to the source of the enriching energy form and the second region that is enriched in the second hydrophilic component relative to the first component is located proximate to the dermal surface on which the mixture is applied; or
    the first region that is enriched in a first lipophilic component of the destabilized mixture relative to the second hydrophilic component of the destabilized mixture is located proximate to the dermal surface on which the mixture is applied and the second region that is enriched in the second hydrophilic component relative to the first lipophilic component is located proximate to the source of the enriching energy form.

5. The applicator device of claim 2, wherein
the first region that is enriched in a first lipophilic component of the destabilized mixture relative to the second hydrophilic component of the destabilized mixture is located proximate to the source of the enriching energy form and the second region that is enriched in the second hydrophilic component relative to the first component is located proximate to the dermal surface on which the mixture is applied; or
the first region that is enriched in a first lipophilic component of the destabilized mixture relative to the second hydrophilic component of the destabilized mixture is located proximate to the dermal surface on which the mixture is applied and the second region that is enriched in the second hydrophilic component relative to the first lipophilic component is located proximate to the source of the enriching energy form.

6. The method of claim 1, wherein:
the first means for generating a destabilizing surface energy is polytetrafluoroethylene, polypropylene, poly (vinyl alcohol), nylon, poly(vinylchloride), poly(ethylene terephthalate), or poly(methyl methacrylate); and/or
the second means for generating an enriching surface energy is copper, aluminum, or chrome.

7. The method of claim 1 comprising:
a) a third destabilizing energy form, wherein the third destabilizing energy form is a weak magnetic field; and/or
b) a second enriching energy form, wherein the second enriching energy form is a weak magnetic field.

8. The method of claim 7, wherein the weak magnetic field of the destabilizing energy form and/or the enriching energy form is generated by a magnetic material with any of the following parameters:
i) a horizontal off-set of between about 1-10 millimetres, 2-8 millimetres, or 3-7 millimetres;
ii) a repetition rate of between about 1-10 elements per centimetre, 1-6 elements per centimeter, or 1.5-4 elements per centimetre;
iii) the poles of the magnetic elements in a particular spatial region are between about 1.0-10 mm apart, or 1.0-5.0 mm apart;
iv) the magnetic flux of each magnetic pole of the magnetic elements is between about 0.1-100 mT, 1-60 mT, or 12-45 mT; and/or
v) the delta flux between the magnetic flux of two adjacent poles of opposite polarity is between about 0.2-200 mT, 20-140 mT, or 20-90 mT.

9. The applicator device of claim 2, wherein:
the first means for generating a destabilising surface energy is polytetrafluoroethylene, polypropylene, poly (vinyl alcohol), nylon, poly(vinylchloride), poly(ethylene terephthalate), or poly(methyl methacrylate); and/or wherein
the second means for generating an enriching surface energy is copper, aluminum, or chrome.

10. The applicator device of claim 2 comprising:
a) a third destabilizing energy form, wherein the third destabilizing energy form is a weak magnetic field; and/or
b) a second enriching energy form, wherein the second enriching energy form is a weak magnetic field.

11. The applicator device of claim 10, wherein the weak magnetic field of the destabilizing energy form and/or the enriching energy form is generated by a magnetic material with any of the following parameters:
i) a horizontal off-set of between about 1-10 millimetres, 2-8 millimetres, or 3-7 millimetres;
ii) a repetition rate of between about 1-10 elements per centimetre, 1-6 elements per centimeter, or 1.5-4 elements per centimetre;
iii) the poles of the magnetic elements in a particular spatial region are between about 1.0-10 mm apart or 1.0-5.0 mm apart;
iv) the magnetic flux of each magnetic pole of the magnetic elements is between about 0.1-100 mT, 1 mT-60 mT, or 12-45 mT; and/or
v) the delta flux between the magnetic flux of two adjacent poles of opposite polarity is between about 0.2-200 mT, 20-140 mT, or 20-90 mT.

\* \* \* \* \*

UNITED STATES PATENT AND TRADEMARK OFFICE
CERTIFICATE OF CORRECTION

PATENT NO. : 10,835,840 B2
APPLICATION NO. : 15/579752
DATED : November 17, 2020
INVENTOR(S) : Jeffrey Edwards et al.

Page 1 of 1

It is certified that error appears in the above-identified patent and that said Letters Patent is hereby corrected as shown below:

In the Claims

Column 30, Line 3, Claim 2 "Pa; and" should read -- Pa, --.

Column 30, Line 34, Claim 3 "Pa; and" should read -- Pa, --.

Column 30, Line 39, Claim 3 "mJ/m$^2$," should read -- mJ/m$^2$, and --.

Column 30, Line 53, Claim 4 "wherein" should read -- wherein: --.

Column 31, Line 3, Claim 5 "wherein" should read -- wherein: --.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*